(12) United States Patent
Kashiwagi

(10) Patent No.: US 7,732,775 B2
(45) Date of Patent: Jun. 8, 2010

(54) APPARATUS AND METHOD FOR RADIATION IMAGING

(75) Inventor: Nobuhiko Kashiwagi, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 302 days.

(21) Appl. No.: 11/865,088

(22) Filed: Oct. 1, 2007

(65) Prior Publication Data

US 2008/0087830 A1 Apr. 17, 2008

(30) Foreign Application Priority Data

Sep. 29, 2006 (JP) ............................. 2006-267910

(51) Int. Cl.
*G01T 1/166* (2006.01)
(52) U.S. Cl. ................................ 250/363.05
(58) Field of Classification Search ............ 250/363.02, 250/363.04, 363.05; 378/37
See application file for complete search history.

(56) References Cited

U.S. PATENT DOCUMENTS 5,452,367 A * 9/1995 Bick et al. ................. 382/128

2002/0141630 A1* 10/2002 Akahori ..................... 382/132
2006/0029268 A1* 2/2006 Endo et al. ................. 382/132
2006/0050944 A1* 3/2006 Takeo et al. ................ 382/132

FOREIGN PATENT DOCUMENTS

| JP | 2005-261846 A | 9/2005 |
| JP | 2006-043187 A | 2/2006 |
| JP | 2006-055419 A | 3/2006 |

* cited by examiner

*Primary Examiner*—David P Porta
*Assistant Examiner*—Marcus H Taningco
(74) *Attorney, Agent, or Firm*—Sughrue Mion, PLLC

(57) ABSTRACT

The radiation imaging apparatus includes a radiation source for irradiating an object, a radiation image detector having a radiation-receiving plane that receives radiation from the radiation source through the object, for detecting a radiation image of the object, a shape information acquiring device for acquiring shape information that represents a shape of the object and a shape information display device that displays the shape information such that it reproduces a position of the object as occurs when the shape information is acquired. The radiation imaging method takes a first radiation image of a first object and generates shape information which represents the shape of the first object, inverts the shape information and displays inverted shape information such that it reproduces a position of the first object and takes a second radiation image of a second object.

20 Claims, 6 Drawing Sheets

APPARATUS AND METHOD FOR RADIATION IMAGING

The entire contents of documents cited in this specification are incorporated herein by reference.

BACKGROUND OF THE INVENTION

The present invention relates to the technical field of radiation imaging (radiation image taking/recording), in particular, to an apparatus and a method for radiation imaging by which the right and left breasts of a subject can be taken with proper register attained between their positions in mammography.

In breast cancer screening, the success rate of early detection that is achieved through physical examination by inspection and palpation only is improved if it is combined with mammography by a radiation image taking apparatus solely intended for breasts (which is hereinafter referred to as a breast imaging apparatus); hence, breast cancer screening that is currently practiced involves the use of a breast imaging apparatus in addition to (or in place of) inspection and palpation.

The breast imaging apparatus comprises an imaging table enclosing a radiation image recording medium (which is hereinafter referred to as an imaging medium); to operate it, the breast is placed on the imaging table, compressed with a press plate, irradiated with a radiation from the press plate side; the radiation transmitted through the breast is received by the imaging medium and its radiation image is taken on the imaging medium.

Diagnosis on radiation images can be performed with greater ease if the radiograph of interest is interpreted in comparison with a reference image. For this reason, mammography is commonly performed with the images of the right and left breasts of a subject being placed side by side for interpretation and diagnosis.

For proper diagnosis, it is preferred that the right and left breasts are imaged symmetrically. To this end, the (imaging) radiologist may adjust the positions of the breasts and the like (perform positioning) while they are compressed with a press plate; however, the current practice of breast radiography largely depends on the skill of the radiologist for proper adjustment of breast position and the like.

JP 2005-261846 A, JP 2006-43187 A, and JP 2006-55419 A show techniques in which, for the purpose of performing diagnosis with the images of the right and left breasts placed side by side, the image data obtained by imaging (taking/recording) the right and left breasts are processed to extract the breast images, which are brought into register and synthesized into a single image.

SUMMARY OF THE INVENTION

However, in each of those technologies, the radiation images taken of the right and left breasts are processed and their positions are brought into register on the mammograms; this is by no means an approach that ensures that the positions of the right and left breasts and the like can be properly adjusted during imaging.

In addition, even in the case where the right and left breasts are placed side by side upon image processing, more appropriate and rapid interpretation of the radiographs and diagnosis can be realized if the right and left breasts are held in appropriate positions during imaging.

An objective, therefore, of the present invention is to solve the aforementioned problems of the prior art by providing a radiation imaging apparatus which, in the case of examining a pair of radiation images in comparison with each other as in mammography, ensures that the position of an object to be imaged later can be easily brought into proper register with the position of the previously imaged object, thereby allowing the two objects in pair to be imaged with proper register between their positions, and which, if applied to the taking of breast radiographs, can image the right and left breasts with their positions being brought into proper register.

Another objective of the present invention is to provide a radiation imaging method that can be implemented in this radiation imaging apparatus.

In order to achieve the above objects, the present invention provides a radiation imaging apparatus, comprising:

a radiation source for irradiating an object;

a radiation image detector for detecting a radiation image of the object, the radiation image detector having a radiation-receiving plane that receives radiation from the radiation source through the object;

a shape information acquiring means for acquiring shape information that represents a shape of the object; and a shape information display means that displays the shape information such that it reproduces a position of the object as occurs when the shape information acquiring means has acquired the shape information.

In the radiation imaging apparatus of the present invention, the shape information acquiring means preferably acquires the shape information as occurs when the object is imaged.

The shape information display means preferably displays the shape information as inverted.

The shape information display means is preferably a display device which causes the shape information and an image of the object to be taken next to be displayed on one display screen.

The shape information display means preferably displays the shape information on an object-supporting plane of the radiation image detector.

In a preferred embodiment, the radiation imaging apparatus further comprising:

a press plate that can be moved closer to or away form the radiation-receiving plane and which compresses the object against an object-supporting plane of the radiation image detector, in which the shape information display means preferably displays the shape information on the press plate.

The shape information acquiring means is preferably a solid-state imaging device.

The shape information acquiring means is preferably the radiation image detector.

The shape information is preferably information about a contour of the object as obtained by analyzing an image information for the object as acquired by the shape information acquiring means.

The object is preferably a breast and the shape information is information about a contour of the breast.

The present invention also provides a radiation imaging method, comprising:

a first imaging step of taking a first radiation image of a first object and generating shape information which represents the shape of the first object;

a display step of inverting the shape information and displaying inverted shape information such that it reproduces a position of the first object in the first imaging step; and a second imaging step of taking a second radiation image of a second object.

In the radiation imaging method, the display step is preferably a step of displaying the shape information in superposition on the second object.

In the first imaging step, the shape information is preferably generated from the image information obtained by imaging the first object as it is in an imaging position with a solid-state imaging device, and the display step is preferably such that while the shape information is displayed on a display device, an image of the second object as obtained by imaging the second object with the solid-state imaging device is simultaneously displayed on the display device.

In the first imaging step, the shape information is preferably generated from the first radiation image of the first object, and the display step is preferably a step of displaying the shape information on an object-supporting plane.

In a preferred embodiment, the radiation imaging method further comprises:

a compressing step of compressing an object against object-supporting plane by means of a press plate before taking a radiation image of the object and in the first imaging step, in which the shape information is preferably generated from the first radiation image of the first object, and the display step is preferably a step of displaying the shape information on the press plate.

It should be noted that the phrase "displayed in superposition" means displaying the shape information in such a way that it can be recognized simultaneously with an object and it is not necessarily required that the shape information be displayed in agreement with the shape of the object.

According to the present invention having the features described above, breasts may be radiographed with the right breast imaged first, then the left breast, in such a way that shape information is acquired when imaging the right breast and at the time when the left breast is being imaged, the shape information for the right breast is presented on a display together with the left breast being imaged, or alternatively, the shape information for the right breast is displayed on an imaging table on which the breast is placed or a press plate that is compressing the breast. Thus, by viewing the shape of the already imaged right breast as it is in a superposed relationship with the left breast to be imaged next, the radiologist can take a radiation image of the left breast while assuring that the positions of the two breasts are easily brought into proper register.

Hence, according to the present invention, radiation images of the two objects in pair can be obtained with their positions being brought into register in a consistent and advantageous manner, as in mammography which involves viewing of the right and left breasts placed side by side.

DETAILED DESCRIPTION OF THE INVENTION

On the pages that follow, the radiation imaging apparatus and method of the present invention are described in detail with reference to the preferred embodiments shown in the accompanying drawings.

Figure 1:
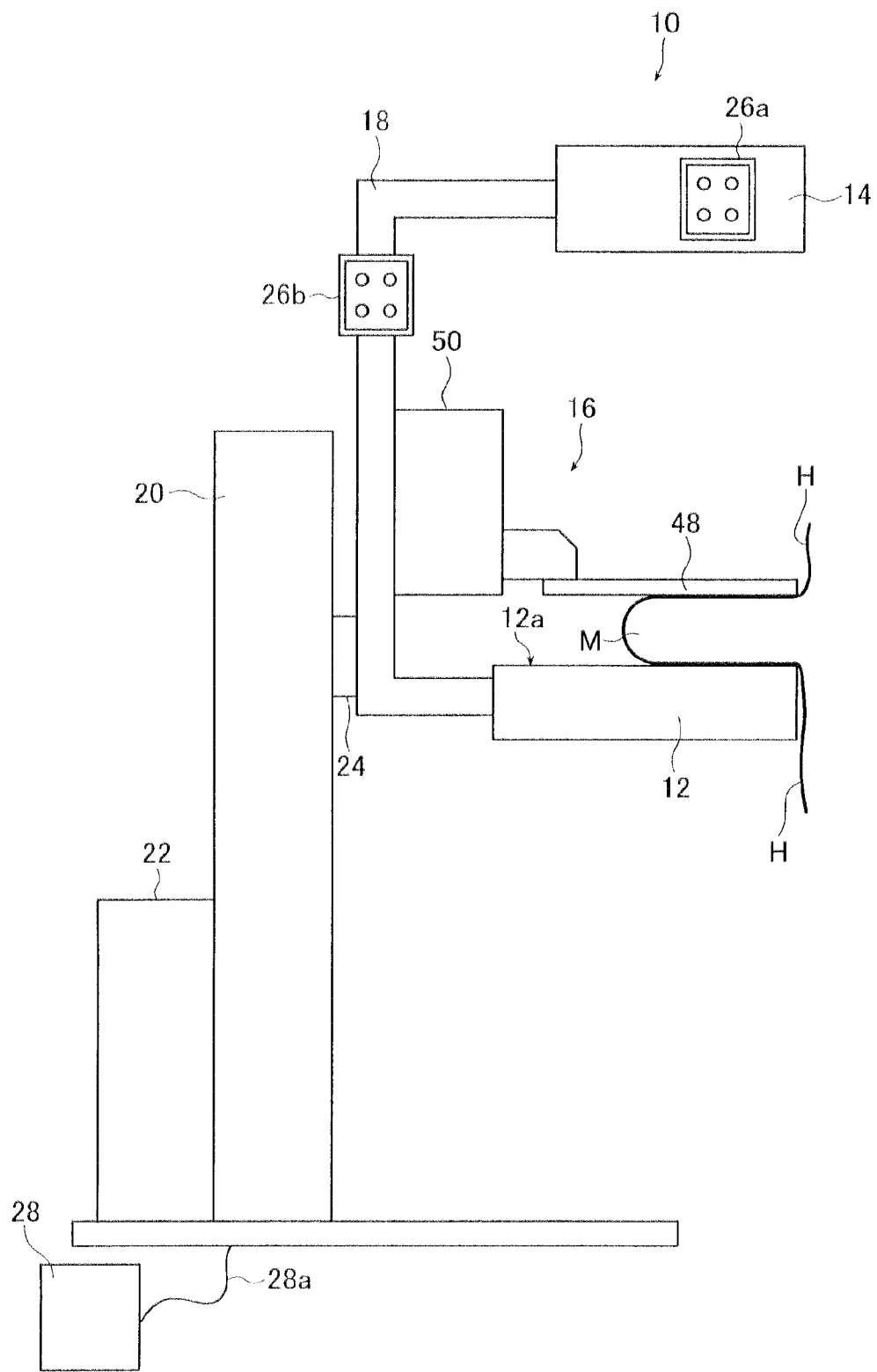
FIG. 1 shows in concept an embodiment of the radiation imaging apparatus of the present invention.

FIG. 1 shows in concept an embodiment of the radiation imaging apparatus of the present invention for implementing the radiation imaging method of the present invention, as it is applied as a breast's radiation image taking apparatus.

As FIG. 1 shows, the breast's radiation image taking apparatus which is generally indicated at 10 (and hereinafter referred to as the mammographic unit 10) is basically composed of an imaging table 12, an irradiating section 14, a compressing means 16, an arm 18, a base 20, and an X-ray irradiating high-voltage power supply 22. The illustrated breast mammographic unit 10 is basically the same as the ordinary breast's radiation image taking apparatus, except that it has the shape information acquiring means and display means that will be described later in detail. In FIG. 1 and other drawings, the symbols M and H represent in concept the breast and chest wall, respectively.

In the illustrated breast imaging apparatus 10, the arm 18 is bent at right angles in two positions to assume a generally C-shaped form; the upper end of the arm 18 is fixed to the irradiating section 14 and the lower end to the imaging table 12, with the compressing means 16 fixed between the irradiating section 14 and the imaging table 12.

Figure 2:
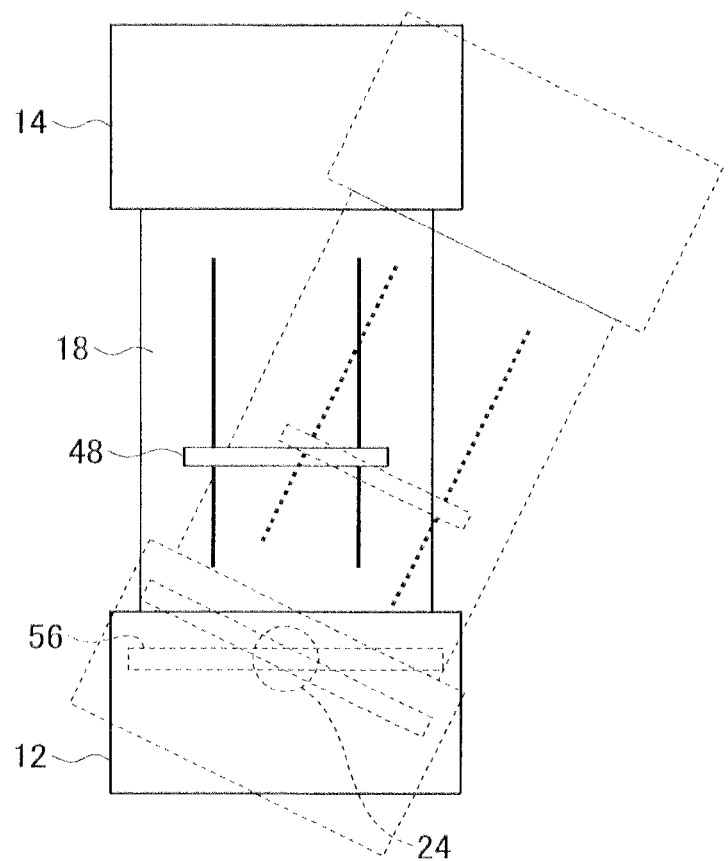
FIG. 2 shows in concept how the radiation imaging apparatus shown in FIG. 1 is operated.

The arm 18 is supported on the base 20 by means of a shaft 24. Built in the interior of the base 20 are a means for rotating the shaft 24, as well as a means for vertically moving it. The arm 18 and, hence, the imaging table 12 and the irradiating section 14 are moved up and down as the shaft 24 is moved up and down by the means that causes it to move vertically; in addition, as shown schematically in FIG. 2, they are rotated as the shaft 24 is rotated by the means that causes it to rotate, whereupon angular adjustment is done to allow for MLO imaging and the like.

The base 20 is fitted with manipulating means 26 (26a and 26b), as well as manipulating means 28 for making a variety of manipulations such as vertically moving and rotating the arm 18 (or shaft 24).

The manipulating means 26a is fitted on a lateral side of the irradiating section 14 and the manipulating means 26b on a lateral side of the arm 18; each of these manipulating means has switches associated with the rotation and vertical movement of the arm 18, a switch that turns on a lamp for illuminating the field of irradiation, and other necessary switches. The manipulating means 28 is a pedal that is connected to the base 20 via a cable 28a and has a switch associated with the vertical movement of a press plate 48 to be described later, a switch associated with the vertical movement of the arm 18, and other necessary switches.

Figure 3:
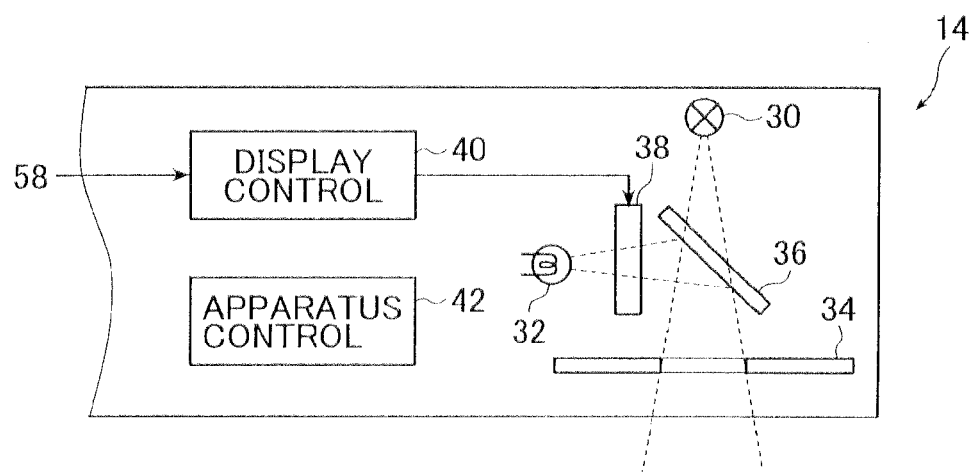
FIG. 3 shows in concept the irradiating section of the radiation imaging apparatus shown in FIG. 1.

The irradiating section 14 is a site for applying a radiation to the breast M and, as shown schematically in FIG. 3, it has a radiation source 30, a projected light source 32, a collimator 34 that regulates the field of irradiation, a mirror 36, a liquid-crystal display device 38 (which is hereinafter designated LCD 38), and a display control means 40.

The irradiating section 14 is also provided with an apparatus control means 42 that manages and controls the overall operation of the mammographic unit 10.

The radiation source 30 may be an ordinary radiation source that is conventionally used in radiation image taking apparatuses. The projected light source 32 is also a known light source used to illuminate the field of irradiation in radiation image taking apparatuses.

The mirror 36 transmits the radiation from the radiation source 30 but reflects the light from the projected light source 32.

In the illustrated case, the radiation source 30 and the projected light source 32 are arranged in optically equivalent positions; to be more specific, the radiation source 30 and the projected light source 32, although located at different positions in a physical space, are arranged in such positions that a linear extension of the optical path of the light reflected from the mirror 36 coincides with the radiation source 30; in other words, the projected light source 32 lies on a straight line that optically connects the radiation source 30 to a detector 56 to be described later.

The LCD 38 is a known liquid-crystal display device of projection type that is used in projectors and the like; of the two breasts to be imaged, right and left, the LCD 38 displays the shape information for the already imaged breast while the other breast is being imaged. The display control means 40 is a control/drive means for the known liquid-crystal display device that acquires shape information from an image processing means to be described later and displays the image represented by the acquired shape information on the LCD 38.

Details of the LCD 38 and the display control means 40 will be described later. In addition to the LCD 38, the present invention can be implemented using other various types of display device that can form projected images. For example, a self-luminescent display device may be used to display the shape information for the already imaged breast and, as will be described later, the thus displayed image may in turn be projected for display on the breast-holding plane 12a.

The compressing means 16 compresses the breast onto the imaging table 12 while it is being imaged; the compressing means 16 has a press plate 48 that compresses the breast onto the imaging table 12 and a means 50 for vertically moving the press plate 48. The press plate 48 is detachably mounted on the vertically moving means 50 and available in two sizes, typically 18×24 cm for a breast of normal size and 24×30 cm for a larger breast.

In the illustrated mammographic unit 10, the press plate 48 and the vertically moving means 50 are basically of known types of a breast press plate and a means for vertically moving it that are provided in a known type of breast's radiation image taking apparatus.

Figure 4:
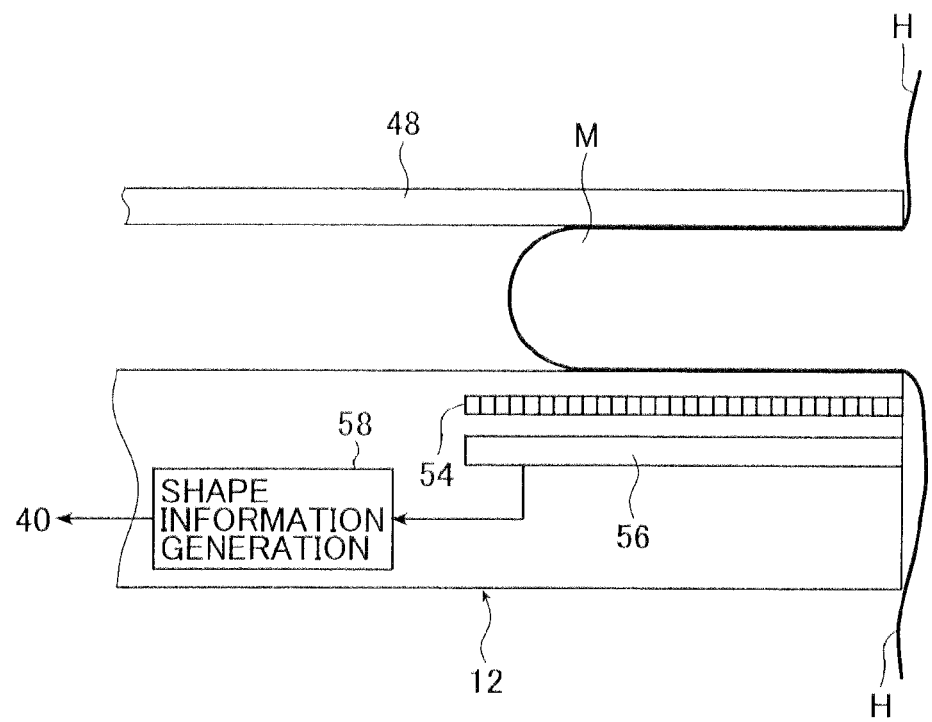
FIG. 4 shows in concept an embodiment of the imaging table of the radiation imaging apparatus shown in FIG. 1.

The imaging table 12 is a hollow case with its upper surface serving as the breast-holding plane 12a; as shown schematically in FIG. 4, it contains a scatter removing grid 54, a detector 56, and a shape information generating means 58 in its interior.

Although not shown, the imaging table 12 contains in it an AEC (automatic exposure control) sensor for measuring the radiation that has passed through the breast in pre-irradiation which is performed prior to the imaging of a breast's radiation image (mammogram) for determining the imaging conditions.

In the illustrated mammographic unit 10, the breast-holding plane 12a of the imaging table 12 constitutes the shape information display means in the present invention.

Specifically, the projected light that has been issued from the projected light source 32 to pass through the LCD 38 and which bears the image displayed on the LCD 38 is projected onto the breast-holding plane 12a, where the projected image is displayed (i.e., the projected light from the LCD 38 produces a visible image). Therefore, the breast-holding plane 12a preferably has a color such as white that enables the projected image to be displayed with great ease.

The scatter removing grid 54 (which is hereinafter referred to simply as the grid 54) is a known means of removing scattered radiation that is installed in a radiation image recording apparatus for the purpose of preventing the admission of a scattered radiation into the detector 56.

The detector 56 is an imaging medium for recording a radiation image.

In the present invention, the detector 56 that can be used is not limited in any particular way and various types of imaging medium (radiation image recording medium) that are employed in radiation image taking/recording apparatuses may be used, as exemplified by the IP (imaging plate) which depends on a stimulable phosphor for radiation image conversion or the flat panel detector which depends on a solid-state detector, a TFT (thin-film transistor) or the like for radiation-to-image conversion (or photoelectric conversion).

If the detector 56 is of a type that uses an IP, it also contains in it an IP reading means that applies exciting light to the IP and photoelectrically reads the photostimulated light that has been issued from the IP in response to the admission of the exciting light.

In the shape information generating means 58, the radiation image of the breast M that has been picked up with the detector 56 is processed to produce an image (image data) that corresponds to the image display by the LCD 38 and which is then supplied to the display control means 40.

More specifically, let us assume for convenience sake that the mammographic unit 10 first takes a radiation image of the right breast M, then the left breast M. In this case, the shape information generating means 58, after taking a radiation image of the right breast M, processes it to extract the skin line (the contour of the breast) and generates an image of the right breast's skin line as the shape information for that breast. Subsequently, the shape information generating means 58 inverts the skin line of the right breast (inverts and reverses right and left the breast's skin line). Further, the shape information generating means 58 converts the image of the inverted right breast's skin line to an image that corresponds to the image display by the LCD 38 and sends it to the display control means 40 in the irradiating section 14.

When the left breast is imaged after the right breast, the display control means 40 causes the LCD 38 to display the skin line (its image) of the right breast supplied from the shape information generating means 58, with the projected image being then displayed on the breast holding plane 12a.

Note that the method of extracting the skin line of the (right) breast is not limited in any particular way and all known methods including the edge detection of an image can be adopted. In one exemplary method, the image is scanned for its density in a horizontal or vertical direction and all positions at which the step difference in density is greater than a specified value are detected and a set of pixels with the step difference in density being greater than the specified value are designated the skin line. Note that the step difference in density may be a preset threshold or positions at which the differential coefficient is greater than a specified value may be designated those positions at which the step difference in density is greater than the specified value.

The method of inverting the image is not limited in any particular way, either, and all known methods including the rearrangement of pixels can be adopted.

On the following pages, the present invention is described in greater detail by explaining how the mammographic unit 10 works.

As already mentioned, in the case under consideration, a radiation image of the right breast of a subject is first taken and thereafter a radiation image of her left breast is taken.

After fitting the vertically moving means 50 with the press plate 48 of a size suitable for the size of the breast M, the radiologist issues a command using the manipulating means 28 and the like, whereupon the vertically moving means 50 lowers the press plate 48 to compress the subject's right breast as it is held between the imaging table 12 (or its breast-holding plane 12a) and the press plate 48.

During the imaging of the right breast (while the first radiation image is taken, or in the first imaging step), all pixels of the LCD 38 are open (to give a white display) and the field of irradiation illuminated with the projected light source 32 is shown on the breast-holding plane 12a.

At the point in time when the compression of the right breast under the press plate 48 has reached a predetermined state, the radiation source 30 is driven to perform pre-irradiation. If pre-irradiation is performed, the imaging conditions (such as the tube voltage and the irradiation time) are set in accordance with the result of this pre-irradiation and the thickness of the breast (i.e., the height of the press plate 48), and in accordance with the thus set imaging conditions, a radiation image of the right breast is taken and recorded on the detector 56.

Note that the projected light source 32 is turned off at the point in time when a command for starting the pre-irradiation is issued. Alternatively, the projected light source 32 may be turned on when the press plate 48 starts to descend and turned off after the passage of a predetermined time.

When the imaging of the right breast ends, the press plate 48 ascends, either automatically or in response to the radiologist's entry of a command, to thereby remove the compression of the right breast.

The radiation image (or its image data) of the right breast as picked up with the detector 56 is sent not only to a specified means for processing this radiation image as exemplified by a work station or server that constitutes a medical image data base but also to the shape information generating means 58.

As already mentioned, the shape information generating means 58 extracts the skin line of the right breast from its radiation image, generates an image of the skin line, inverts it, and converts the inverted image to one that corresponds to the image display by the LCD 38.

In this case, the shape information generating means 58 generates the skin line image in such a way that in the projected image from the LCD 38 that is displayed on the breast-holding plane 12a of the imaging table 12, the skin line of the right breast is in the same position as the right breast lying on the breast-holding plane 12a. In other words, the skin line image is generated in such a way as to reproduce the right breast lying on the breast-holding plane 12a.

As already mentioned, the image of the skin line of the right breast is sent to the display control means 40 in the irradiating section 14.

The display control means 40 supplied with the skin line image causes the LCD 38 to display the supplied image of the skin line of the right breast on a specified timing such as between the removal of compression from the first imaged right breast and the start of compression on the yet to be imaged left breast. Therefore, the projected light that has been issued from the projected light source 32 to pass through the LCD 38 now bears the image of the skin line of the right breast and the projected image of the skin line is displayed (projected) on the breast holding plane 12a of the imaging table 12.

The left breast is imaged in the same way as the first imaged right breast; the radiologist issues a command using the manipulating means 28 and the like, whereupon the vertically moving means 50 lowers the press plate 48 to compress the subject's left breast as it is held between the imaging table 12 (or its breast-holding plane 12a) and the press plate 48.

Figure 5:
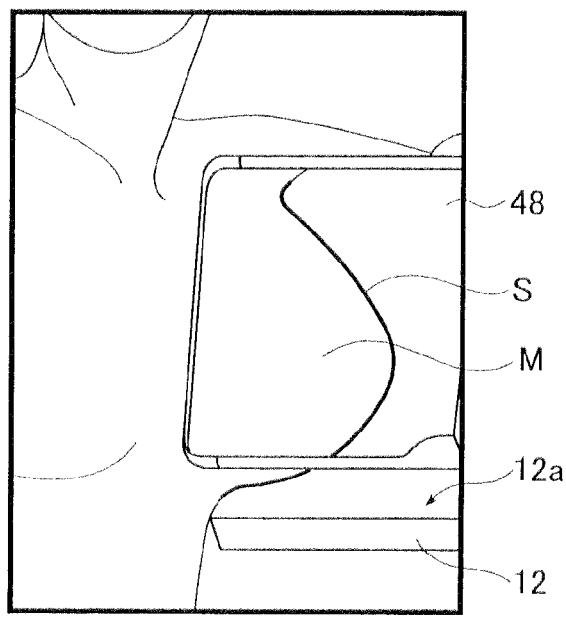
FIG. 5 shows in concept how the radiation imaging apparatus shown in FIG. 1 works.

In this case which is shown schematically in FIG. 5, the breast holding plane 12a shows a display of the skin line S of the first imaged right breast. In other words, the skin line S reproducing the first imaged right breast is displayed in superposition on the left breast yet to be imaged.

Thus, the radiologist who is compressing the left breast can simultaneously look at the skin line of the first imaged right breast to ensure that the left breast is appropriately positioned (i.e., has its position and shape adjusted in agreement with the skin line of the right breast), thereby enabling the radiation images of the right and left breasts to be taken with proper register attained in terms of position and shape. As a result, the present invention allows consistent taking of mammograms that record the right and left breasts sufficiently symmetric to each other that the physician can interpret them accurately in an advantageous way.

The subsequent steps are the same as in the first imaging of the right breast; at the point in time when the compression of the left breast has reached a predetermined state, pre-irradiation is performed to set the imaging conditions; further, in accordance with the thus set imaging conditions, a radiation image of the left breast is picked up with the detector 56 and the recorded radiation image of the left breast is sent to the specified image processing means already described above. When the imaging of the left breast ends, the press plate 48 ascends, either automatically or in response to the radiologist's entry of a command, to thereby remove the compression of the left breast.

During the imaging of the left breast (in the second imaging step), no skin line image is created, so the radiation image of the left breast that has been recorded is not supplied to the shape information generating means 58.

In the illustrated mammographic unit 10, the breast holding plane 12a of the imaging table 12 is utilized as a display means on which the image represented by the shape information about the breast (the skin line of the breast) is displayed.

However, the present invention is by no means limited to that particular embodiment and in place of the imaging table 12, the upper surface of the press plate 48 may be utilized as a display means, onto which the image being displayed by the LCD 38 is projected.

It should be noted here that in the breast's radiation image taking apparatus, the press plate 48 is usually colorless and transparent, so in order to display a projected image using the press plate 48 as a display means, it cannot be colorless and transparent but needs to have a transparent milky white color, a matted finish or other features that permit display of a projected image.

It should also be noted that the shape information about the breast is in no way limited to the illustrated skin line.

If desired, the radiation image of the first viewed left breast may be inverted to generate shape information for subsequent display. Alternatively, the skin line or radiation image of the breast may be graphically represented by a simple figure, such as a generally U-shaped figure, a semicircular figure or a generally semi-elliptical figure, which can be substituted for shape information to display an image that is represented by one of these simplified figures.

In addition, the shape information is by no means limited to the type that has the information for the entire part of the breast; if desired, the skin line of only the mammary papilla or an image that graphically represents the mammary papilla by a simplified figure may be used as shape information to be displayed.

It should also be noted that the method of image display of the shape information on the breast-holding plane 12a or the press plate 48 is in no way limited to the illustrated case of utilizing the LCD 38 (the means of generating a projected image).

Figure 6:
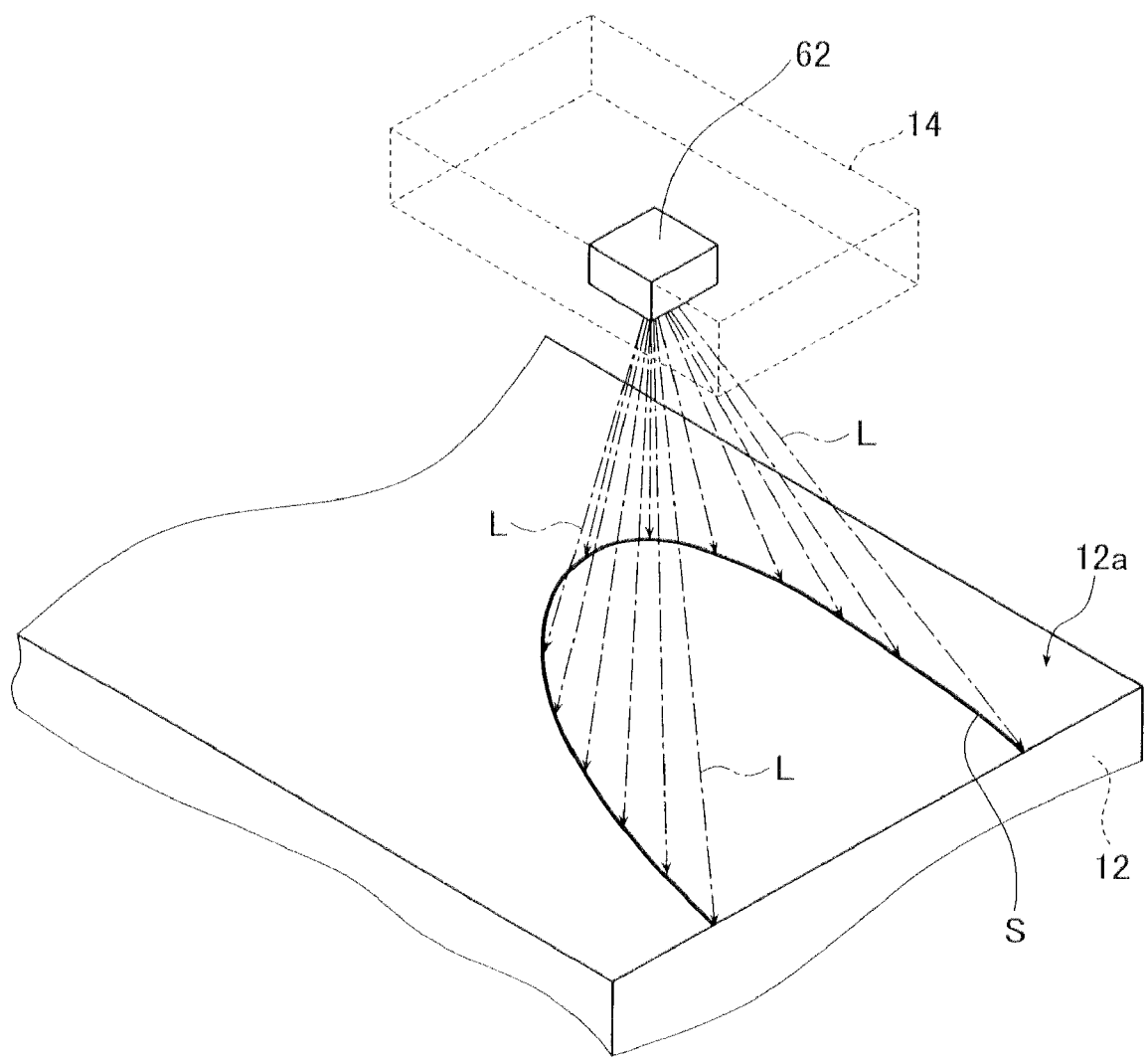
FIG. 6 shows in concept another embodiment of the radiation imaging apparatus of the present invention.

Another example that can be adopted is shown schematically in FIG. 6; the lower surface of the irradiating section 14 is fitted with a laser beam irradiating means 62 that issues a laser beam L and deflects it two-dimensionally; the laser beam L from the laser beam irradiating means 62 is used to display the skin line S of the breast M or an image representing the breast M in a simplified figure is displayed on the breast-holding plane 12a (or the press plate 48).

In the breast imaging apparatus 10 shown in FIG. 1 and other drawings, the detector 56 is utilized as the shape information acquiring means to generate shape information from the radiation image of the right breast (the first imaged breast), and the breast-holding plane 12a or the press plate 48 is utilized as a constituent of the shape information display means.

The present invention is by no means limited to that particular design; if desired, a solid-state imaging device such as a CCD camera may be used as the shape information acquiring means and a display may be used as the shape information display means.

Figure 7:
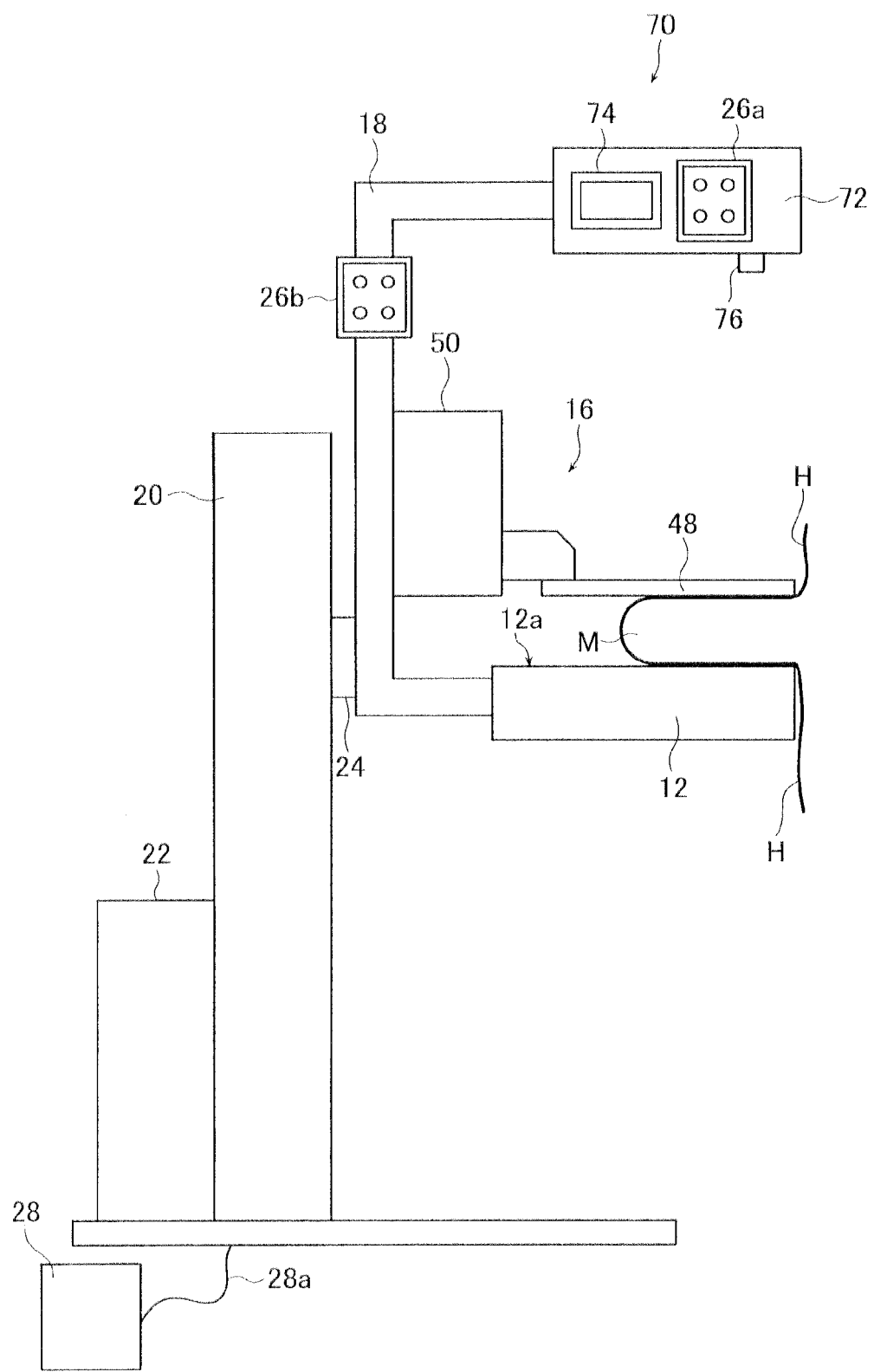
FIG. 7 shows in concept another embodiment of the radiation imaging apparatus of the present invention.

FIG. 7 shows in concept a breast's radiation image taking apparatus that uses both a CCD camera and a display and which is generally indicated by 70. On the following pages, this apparatus is designated the mammographic unit 70.

The mammographic unit 70 shown in FIG. 7 has many constituents in common with the already described mammographic unit 10, so like parts are identified by like numerals and the following explanation is mostly directed to the unlike parts.

Like the above-described mammographic unit 10, the mammographic unit 70 is designed for taking a radiation image of the breast and is basically composed of an imaging table 12, an irradiating section 72, a compressing means 16, an arm 18, and a base 20.

The imaging table 12, the compressing means 16, the arm 18 and the base 20 in the mammographic unit 70 are essentially the same as in the above-described mammographic unit 10, except that the imaging table 12 does not have the shape information generating means 58 in its interior; hence, those parts of the mammographic unit 70 will not be described in detail.

As shown schematically in FIG. 7, the irradiating section 72 of the mammographic unit 70 has a display 74 provided on its lateral side and a CCD camera 76 provided on its lower surface in an area near the position from which a radiation is issued.

Figure 8:
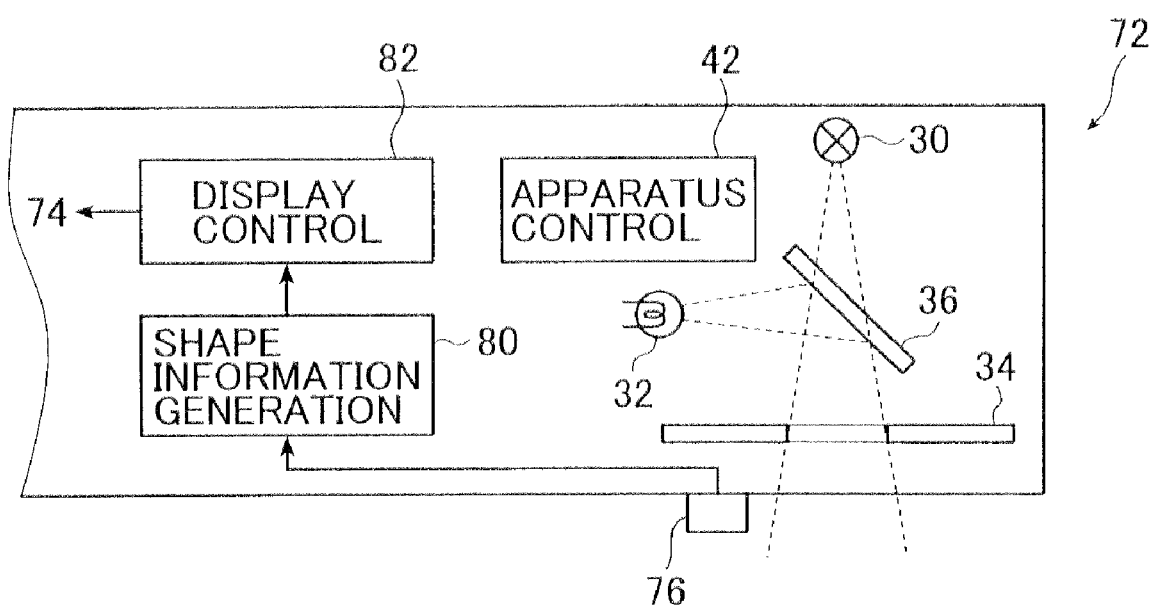
FIG. 8 shows in concept an embodiment of the irradiating section of the radiation imaging apparatus of the present invention.

FIG. 8 shows the irradiating section 72 in concept.

As is clear from FIG. 8, the irradiating section 72 of the mammographic unit 70 has the same construction as the irradiating section 14 of the already-described mammographic unit 10, except that it does not have the LCD 38 or the display control means 40 associated with the LCD 38 but that it has the display 74 and the CCD camera 76, as well as a shape information generating means 80 and a display control means 82 associated with the display 74.

The CCD camera 76 is a known imaging unit using a CCD sensor and it takes a view of a specified region of the breast holding plane 12a that covers the field of irradiation with the radiation source 30. The display 74 is also a known display unit and all known types of display unit such as LCD and CRT may be adopted. Note that in addition to the CCD camera 76, various types of solid-state imaging devices can be used in the present invention.

In the mammographic unit 70, the CCD camera 76 and the display 74 may be of a monochromatic or colored type; however, they are preferably of a colored type for various reasons including the ease with which the image represented by shape information can be sufficiently distinguished from the breast to facilitate positioning of the breast to be imaged later.

In the illustrated case, the CCD camera 76 and the radiation source 30 are disposed at different positions but in order to obtain shape information that is more faithful to the radiation image of the first recorded right breast, the CCD camera 76 and the radiation source 30 may be arranged in optically equivalent positions.

For example, similar to the breast imaging apparatus 10 shown in FIG. 1, a mirror 36 that transmits a radiation may be provided and the radiation source 30 and the CCD camera 76, although located at different positions in a physical space, may be arranged in such positions that a linear extension of the return path of reflected light from the mirror 36 coincides with the radiation source 30, whereby the mirror image created with that mirror allows the CCD camera 76 to take a view of the breast-holding plane 12a. In other words, the CCD camera 76 lies on a straight line that optically connects the radiation source 30 to the detector 56.

The shape information generating means 80 generates the shape information about the breast by processing the image picked up with the CCD camera 76; it also converts the same image from the CCD camera 76 to an image (image data) that corresponds to the image display by the display 74 and supplies it to the display control means 82.

The display control means 82 is a known display drive/control means by which the image as supplied from the shape information generating means 80 is presented on the display 74 and which is selected in accordance with the specific type of the display 74 used.

More specifically, as in the above-described mammographic unit 10, let us assume for convenience sake that the mammographic unit 70 first takes a radiation image of the right breast M, then the left breast M. The CCD camera 76, while the detector 56 is picking up a radiation image of the right breast, takes a still image of the right breast.

The image of the right breast as picked up by the CCD camera 76 is supplied to the shape information generating means 80. The shape information generating means 80 processes the supplied image of the right breast to extract its skin line as in the previous case, and generates the image of the right breast's skin line, then inverts it to produce an image that corresponds to the image presentation by the display 74.

On the other hand, when imaging the left breast, the CCD camera 76 takes a moving picture and supplies it to the shape information generating means 80. The shape information generating means 80 then converts the supplied moving picture of the left breast to a moving picture that corresponds to image reproduction by the display while, at the same time, it combines this moving picture with the already generated skin line of the right breast and sends the composite image to the display control means 82. In accordance with this composite image, the display control means 82 drives the display 74 for image display.

As in the previous case, extraction of the skin line and image inversion may be performed by any known means. The shape information need not be the skin line but it may be replaced by a radiation image, a simplified image or the like, as in the previous case.

On the following pages, the present invention is described in greater detail by explaining how the mammographic unit 70 works.

As in the previous case, it is assumed here that a radiation image of the right breast of a subject is first taken and thereafter a radiation image of her left breast is taken. Similarly, after fitting the press plate 48 of a size suitable for the size of the breast M, the radiologist issues a relevant command, whereupon the vertically moving means 50 lowers the press plate 48 to compress the subject's right breast. In addition, the field of irradiation illuminated with the projected light source 32 is shown on the breast-holding plane 12*a*.

At the point in time when the compression of the right breast under the press plate 48 has reached a predetermined state, the radiation source 30 is driven to perform pre-irradiation to set the imaging conditions, and in accordance with the thus set imaging conditions, a radiation image of the right breast is taken and recorded on the detector 56.

When the imaging of the right breast ends, the press plate 48 ascends, either automatically or in response to the radiologist's entry of a command, to thereby remove the compression of the right breast.

After the right breast was compressed to the predetermined state but before removal of the compression gets started, the CCD camera 76 takes a still image and sends it to the shape information generating means 80.

As already mentioned, the shape information generating means 80 generates an image of the skin line of the right breast, inverts it, converts the inverted image to one that corresponds to the image presentation by the display 74, and stores that image.

When the imaging of the right breast ends, a radiation image of the left breast is taken.

The left breast is imaged in the same way as the first imaged right breast; the radiologist issues a command using the manipulating means 28 and the like, whereupon the vertically moving means 50 lowers the press plate 48 to compress the subject's left breast as it is held between the imaging table 12 and the press plate 48.

Here, in the irradiating section 72, the CCD camera 76 starts to take a moving picture of the left breast on a specified timing such as between the end of imaging of the right breast and the start of compressing of the left breast, whereas the shape information generating means 80 converts the moving picture of the left breast to a moving picture that corresponds to the image presentation by the display 74 while, at the same time, it combines this moving picture with the already generated skin line of the right breast and causes the display 74 to present that composite image on the display 74. Thus, in the mammographic unit 70, while the left breast to be radiographed after the right breast is being compressed, the moving picture of the left breast and the image of the already generated skin line of the right breast are displayed in a superposed relationship. The phrase "displayed in a superposed relationship" means that the skin line of the right breast which is the already acquired shape information and the next imaged left breast are displayed on the same screen so that they can be recognized simultaneously.

The skin line image of the right breast has been taken with the CCD camera 76 which is currently taking the moving picture of the left breast; in other words, this skin line reproduces the right breast that was imaged with the CCD camera 76 after taking the radiation image of the right breast.

Thus, as in the previous case, the radiologist who is compressing the left breast can simultaneously look at the skin line of the first imaged right breast to ensure that the left breast is appropriately positioned, thereby enabling the radiation images of the right and left breasts to be taken with proper register attained. As a result, the present invention allows consistent taking of mammograms that record the right and left breasts sufficiently symmetric to each other that the physician can interpret them accurately in an advantageous way.

The subsequent steps are the same as in the first imaging of the right breast; at the point in time when the compression of the left breast has reached a predetermined state, pre-irradiation is performed to set the imaging conditions; further, in accordance with the thus set imaging conditions, a radiation image of the left breast is picked up with the detector 56 and the recorded radiation image of the left breast is sent to the specified image processing means already described above. When the imaging of the left breast ends, the press plate 48 ascends, either automatically or in response to the radiologist's entry of a command, to thereby remove the compression of the left breast.

During the imaging of the left breast, the shape information generating means 80 does not generate any shape information.

In the foregoing cases, the right breast (the breast to be imaged first) is compressed while it is handled for generating the skin line (acquiring shape information) but the present invention is in no way limited to this particular embodiment. If desired, a skin line may be generated for the right breast in an uncompressed state and prior to compressing the left breast (the breast to be imaged later), the skin line of the uncompressed right breast is shown on the breast-holding plane 12*a* or the display 74 so that the skin line of the first radiographed right breast is displayed in superposition on the yet to be imaged left breast. This enables position check and register to be performed with reference to the uncompressed breast, thereby assisting in the positioning of the breast and allowing the imaging of radiation images with proper register attained between the right and left breasts.

Alternatively, in the imaging of the right breast, two skin lines of it may be generated, one before compression and the other after compression, and prior to compressing the left breast, the skin line of the uncompressed right breast is displayed in superposition on the uncompressed left breast and, on a predetermined timing associated with the start of compressing (or on a timing in response to the entry of a command by the radiologist), the display of the skin line is changed to such a mode that the skin line of the compressed right breast is displayed in superposition on the left breast to be compressed.

In diagnosis by mammography, it is sometimes required to compare the current mammogram with the previously taken mammogram to secure correct interpretation and diagnosis.

To meet this need, the present invention may be so adapted that shape information such as the skin line of a breast that has been acquired during the taking of its radiation image is stored in a data base or the like and in subsequent taking of breast's radiation images, the past shape information is retrieved for display. In an exemplary case, while the right breast (the breast to be imaged first) of a subject is compressed, the shape information about the right breast of the same subject that was obtained in the past may be retrieved and shown on the breast-holding plane 12a or the display 74 so that the image represented by this past shape information is displayed in superposition on the right breast which is yet to be radiographed.

Therefore, in the case of utilizing the shape information that was obtained in the past, there is no need to invert right and left the image represented by the shape information such as a skin line and it is preferred to acquire shape information such as the skin lines of both right and left breasts in the process of taking a radiation image. If desired, this case may be modified such that the directions of rotation as in craniocaudal (CC) or medio-lateral and oblique (MLO) imaging are recognized automatically to allow for selection of an image to be displayed.

According to this method, when diagnosing the breast of a subject by comparing it with a mammogram taken in the past, the physician, while looking at the image represented by shape information such as the skin line of the breast imaged in the past, can perform positioning of the yet to be radiographed breast, whereby radiation images of the two breasts can be taken with proper register attained. As a result, the present invention allows consistent taking of mammograms that feature an agreement between the breast that was imaged in the past and the breast that has been imaged for diagnosis and which enable the physician to interpret them accurately in an advantageous way.

According to the basic assumption of the present invention, two corresponding images making a pair, such as radiation images of the right and left breasts or the present and past radiation images, are taken and shape information is displayed in correspondence with the radiation image that is to be taken at a later time.

Consider, for example, the case where radiation images of breasts are taken by MLO imaging only; the procedure goes like MLO imaging of the left breast and acquisition of shape information about it → display of the shape information and MLO imaging of the right breast → change of subjects. If MLO imaging is followed by CC imaging, the procedure goes like MLO imaging of the left breast and acquisition of shape information about it → display of the shape information and MLO imaging of the right breast → CC imaging of the left breast and acquisition of shape information about it → display of the shape information and CC imaging of the right breast → change of subjects.

Consider the other case where the shape information to be displayed is about an image that was taken in the past; if MLO imaging is to be performed, the procedure goes like acquisition of shape information about the past MLO imaging of the left breast → display of the shape information and MLO imaging of the left breast.

In the foregoing cases, in order to take radiation images, the shape information about the breast is presented on the breast holding plane 12a or a display; however, this is not the sole case of the present invention and various other embodiments are possible by making use of the shape information about the breast that was radiographed first.

One such example is described below on the same assumption as taken in the previous case, that is, a radiation image of the right breast is taken first. As in the previous case, shape information such as the skin line of the right breast may be acquired and stored; then, shape information about the left breast to be taken next is acquired and compared with the stored shape information about the right breast; the position of the left breast, as well as the positions of the radiation source and the detector (and the scatter removing grid) are so modified as to minimize the offset between the positions of the two breasts on the detector.

Specifically, the press plate and the breast holding plane may be adapted to be movable in a direction parallel to the breast holding plane (but the detector and other parts are fixed); alternatively, the radiation source and the detector may be adapted to be movable in that direction. If desired, both groups may be adapted to be movable.

Given this apparatus design, a radiation image of the right breast is first taken, with shape information such as the skin line of the right breast before and/or after compression being acquired and stored, as in the previous case. Then, before taking a radiation image of the left breast, shape information such as the skin line of the left breast is acquired by the same means as applied to the first imaged right breast.

When the shape information about the left breast has been acquired, as exemplified by generation of its skin line, the previously stored shape information about the right breast is compared with the shape information about the left breast and the positional offset between the two breasts on the detector is detected. Such positional offset may be detected by any known means such as comparison of edge positions.

When the positional offset has been detected in the shape information for the two breasts, the positions of the press plate and the breast-holding plane or those of the radiation source and the detector are so adjusted as to minimize the positional offset; thereafter, a radiation image of the left breast is taken.

The same procedure as the above may of course be followed to correct any positional offset between the breast that was radiographed in the past and the breast of the same subject that is yet to be radiographed.

A radiation imaging apparatus that may be used in this alternative embodiment comprises a radiation source for irradiating an object, a radiation image detector having a radiation-receiving plane that receives the radiation from the radiation source through the object for detecting a radiation image of the object, a shape information acquiring means for acquiring shape information that represents the shape of the object, a memory means for storing the shape information, a positional offset detector means by which the positional offset as occurs on the radiation image detector between a first object and a second object to be radiographed after the first object is detected from the shape information about the first object that is stored in the memory means and the shape information about the second object, and a moving means that adjusts the relative positions of the second object and the radiation image detector so as to minimize the positional offset that has been detected by the positional offset detector means.

A radiation imaging method that may also be used in the alternative embodiment under consideration comprises a first imaging step of taking a radiation image of the first object and generating shape information that represents the shape of the first object, a second shape information generating step in which the shape information about a second object to be radiographed after the first object is generated in the same manner as the shape information that is generated in the first imaging step, a detection step in which the shape information about the second object and the shape information about the first object as inverted right and left are compared to detect any positional offset that occurs on the radiation image detector between the two kinds of shape information, and a moving step of adjusting the relative positions of the second object and the radiation image detector so as to minimize the positional offset between the two kinds of shape information that has been detected in the detection step.

While the radiation imaging apparatus and method of the present invention have been described above in detail, the present invention is by no means limited to the foregoing embodiments and various improvements and modifications can of course be made without departing from the scope and spirit of the present invention.

What is claimed is:

1. A radiation imaging apparatus, comprising:
   a radiation source for irradiating an object;
   a radiation image detector for detecting a radiation image of said object, said radiation image detector having a radiation-receiving plane that receives radiation from said radiation source through said object;
   a shape information acquiring means for acquiring shape information that represents a shape of said object; and
   a shape information display means that displays said shape information such that it reproduces a position of said object as occurs when said shape information acquiring means has acquired said shape information,
   wherein said shape information display means displays said shape information on an object-supporting plane of said radiation image detector.

2. The radiation imaging apparatus according to claim 1, wherein said shape information acquiring means is for acquiring said shape information of said object when said object is imaged.

3. The radiation imaging apparatus according to claim 1, wherein said shape information display means is for inverting said shape information and displaying inverted shape information.

4. The radiation imaging apparatus according to claim 1, wherein said shape information display means is for displaying said shape information and an image of said object to be taken next simultaneously on one display screen.

5. The radiation imaging apparatus according to claim 1, wherein said shape information acquiring means is a solid-state imaging device.

6. The radiation imaging apparatus according to claim 1, wherein said shape information acquiring means is said radiation image detector.

7. The radiation imaging apparatus according to claim 1, wherein said shape information acquiring means is for acquiring said shape information which is information about a contour of said object as obtained by analyzing an image information for said object as acquired by said shape information acquiring means.

8. The radiation imaging apparatus according to claim 1, wherein said shape information acquiring means is for acquiring said shape information which is information about a contour of a breast of said object.

9. A radiation imaging apparatus comprising:
   a radiation source for irradiating an object;
   a radiation image detector for detecting a radiation image of said object, said radiation image detector having a radiation-receiving plane that receives radiation from said radiation source through said object;
   a shape information acquiring means for acquiring shape information that represents a shape of said object; and
   a shape information display means that displays said shape information such that it reproduces a position of said object as occurs when said shape information acquiring means has acquired said shape information, and
   a press plate that can be moved closer to or away from said radiation-receiving plane and which compresses said object against an object-supporting plane of said radiation image detector,
   wherein said shape information display means displays said shape information on said press plate.

10. The radiation imaging apparatus according to claim 9, wherein said shape information acquiring means is for acquiring said shape information of said object when said object is imaged.

11. The radiation imaging apparatus according to claim 9, wherein said shape information display means is for inverting said shape information and displaying inverted shape information.

12. The radiation imaging apparatus according to claim 9, wherein said shape information display means is for displaying said shape information and an image of said object to be taken next simultaneously on one display screen.

13. The radiation imaging apparatus according to claim 9, wherein said shape information acquiring means is a solid-state imaging device.

14. The radiation imaging apparatus according to claim 9, wherein said shape information acquiring means is said radiation image detector.

15. The radiation imaging apparatus according to claim 9, wherein said shape information acquiring means is for acquiring said shape information which is information about a contour of said object as obtained by analyzing an image information for said object as acquired by said shape information acquiring means.

16. The radiation imaging apparatus according to claim 9, wherein said shape information acquiring means is for acquiring said shape information which is information about a contour of a breast of said object.

17. A radiation imaging method, comprising:
   a first imaging step of taking a first radiation image of a first object and generating shape information which represents the shape of said first object;
   a display step of inverting said shape information and displaying inverted shape information such that it reproduces a position of said first object in said first imaging step; and
   a second imaging step of taking a second radiation image of a second object, wherein,
   in said first imaging step, said shape information is generated from said first radiation image of said first object, and
   said display step is a step of displaying said shape information on an object-supporting plane.

18. The radiation imaging method according to claim 17, wherein said display step is a step of displaying said shape information in superposition on said second object.

19. The radiation imaging method according to claim 17, wherein,
   in said first imaging step, said shape information is generated from said image information obtained by imaging said first object as it is in an imaging position with a solid-state imaging device, and
   said display step is such that while said shape information is displayed on a display device, an image of said second object as obtained by imaging said second object with said solid-state imaging device is simultaneously displayed on said display device.

20. A radiation imaging method comprising:
   a first imaging step of taking a first radiation image of a first object and generating shape information which represents the shape of said first object;
   a display step of inverting said shape information and displaying inverted shape information such that it reproduces a position of said first object in said first imaging step; and a second imaging step of taking a second radiation image of a second object; and a compressing step of compressing an object against object-supporting plane by means of a press plate before taking a radiation image of said object and in said first imaging step, wherein said shape information is generated from said first radiation image of said first object, and said display step is a step of displaying said shape information on said press plate.

* * * * *